(12) United States Patent
Gallis et al.

(10) Patent No.: US 7,255,852 B2
(45) Date of Patent: Aug. 14, 2007

(54) PRECIPITATED SILICA PRODUCT, DENTIFRICES CONTAINING SAME, AND PROCESSES

(75) Inventors: Karl W. Gallis, Belcamp, MD (US); Mark E. Wozniak, Bel Air, MD (US); John A. Kostinko, Bel Air, MD (US)

(73) Assignee: J.M. Huber Corporation, Edison, NJ (US)

( * ) Notice: Subject to any disclaimer, the term of this patent is extended or adjusted under 35 U.S.C. 154(b) by 195 days.

(21) Appl. No.: 10/677,294

(22) Filed: Oct. 3, 2003

(65) Prior Publication Data

US 2004/0161390 A1   Aug. 19, 2004

Related U.S. Application Data

(63) Continuation-in-part of application No. 10/366,604, filed on Feb. 14, 2003, now Pat. No. 6,946,119.

(51) Int. Cl.
*A61K 8/00* (2006.01)
*A61Q 11/00* (2006.01)
*C01B 33/12* (2006.01)

(52) U.S. Cl. ............................. 424/54; 424/49; 424/52; 516/82; 516/113; 423/335; 423/339; 51/308

(58) Field of Classification Search ...................... None
See application file for complete search history.

(56) References Cited

U.S. PATENT DOCUMENTS

| | | | |
|---|---|---|---|
| 2,601,235 A | 6/1952 | Alexander et al. | |
| 2,731,326 A | 1/1956 | Alexander et al. | |
| 2,885,366 A | 5/1959 | Iler | |
| 5,266,306 A | 11/1993 | Ohtsuki et al. | |
| 5,447,704 A | 9/1995 | Aldcroft et al. | |
| 5,647,903 A * | 7/1997 | McGill et al. | 424/49 |
| 5,897,849 A | 4/1999 | Alcaraz et al. | |
| 5,968,470 A | 10/1999 | Persello | |
| 5,989,524 A * | 11/1999 | Dromard et al. | 424/49 |
| 6,159,277 A | 12/2000 | Tanaka et al. | |
| 6,294,106 B1 | 9/2001 | Pryor | |
| 6,342,193 B1 | 1/2002 | Tanaka et al. | |
| 6,365,522 B1 | 4/2002 | Pryor | |
| 6,471,948 B1 | 10/2002 | Adamy et al. | |

FOREIGN PATENT DOCUMENTS

| | | |
|---|---|---|
| EP | 0236070 B1 | 3/1992 |
| EP | 0666832 B2 | 7/2002 |
| WO | WO 93/33007 | * 11/1993 |

* cited by examiner

*Primary Examiner*—Frederick Krass
(74) *Attorney, Agent, or Firm*—Carlos Nieves; Raymond Hoch

(57) ABSTRACT

Precipitated silica comprising porous silica particles having a cumulative surface area for all pores having diameters greater than 500 Å of less than 8 m²/g, as measured by mercury intrusion, and a percentage cetylpyridinium chloride (% CPC) Compatibility of greater than about 55%. The precipitated silica product is especially well-adapted for use in dentifrices containing cetylpyridinium chloride, which do not attach to the low surface area silica product in a meaningful level and thus remain available for antimicrobial action. Processes for making the silica product are also provided.

30 Claims, 2 Drawing Sheets

PRECIPITATED SILICA PRODUCT, DENTIFRICES CONTAINING SAME, AND PROCESSES

CROSS-REFERENCE TO RELATED APPLICATIONS

This patent application is a continuation-in-part of prior U.S. patent application Ser. No. 10/366,604, filed Feb. 14, 2003 now U.S. Pat. No. 6,946,119, which is hereby incorporated herein by reference in its entirety.

BACKGROUND OF THE INVENTION

1. Field of the Invention

This invention relates to precipitated amorphous silica, and processes for making it. The precipitated silica is especially well-adapted for use in dentifrices containing cetylpyridinium chloride.

2. Description of the Related Art

Modern dentifrices often contain an abrasive substance for controlled mechanical cleaning and polishing of teeth, and optionally a chemical cleaning agent, among other common ingredients, such as humectants, flavors, therapeutic ingredients, such as an anticaries agent, rheology control agents, binders, preservatives, colors, and sudsing agents, among others. Oral care products also often contain therapeutic agents, such as anti-microbial agents. Cetylpyridinium chloride ("CPC") is an anti-microbial agent used for this purpose, such as in mouthwashes and toothpastes. There is an increased desire among dentifrice manufacturers to incorporate anti-microbial agents in dentifrice applications for the control of malodor and/or other therapeutic action, with CPC being one of the more favored. It is cost effective and generally recognized as safe. By contrast, some alternative anti-microbial agents currently being used in dentifrices have come under increasing scrutiny for possible contribution to the increased resistance of some bacterial strains to antibiotics. CPC is not considered to contribute to this health problem.

CPC is a cationic ("positively") charged compound. CPC's antimicrobial action is generally understood to result from its ability to bind to anionically ("negatively")-charged protein moieties on bacterial cells present in the mouth. This CPC attachment mechanism results in a disruption of normal cellular function of bacteria and contributes to the prevention of plaque formation and other bacterial actions.

A problem encountered in CPC usage in dentifrices has been that CPC tends to indiscriminately bind to negatively-charged surfaces. In particular, co-ingredients of toothpaste formulations having negatively-charged surfaces also may bind to CPC before it performs any antimicrobial action. Once bound to these nontargeted surfaces, the CPC is generally unavailable to perform any meaningful antimicrobial action.

In this regard, silica is often used as an abrasive in dentifrices. For instance, silica's abrasive action is used for pellicle removal from teeth. Most conventional silicas used in dentifrices have negatively-charged surfaces. Consequently, CPC adsorbs onto such conventional silica powders. For reasons explained above, the adsorption of CPC upon silica or other co-ingredients of the dentifrice is highly undesirable.

U.S. Pat. No. 6,355,229 describes a CPC compatible dentifrice formulation containing guar hydroxypyropyl-trimonium chloride. The guar complex has a higher affinity toward binding to negatively-charged species. It preferentially binds to anionic components leaving CPC free to bind to plaque.

U.S. Pat. No. 5,989,524 describes a silica that is compatible with flavors obtained by treating the surface of the silica originating from the reaction of an alkali metal silicate with an inorganic or organic acidic agent with the aid of an organic compound capable of developing hydrogen or ionic bonds with the Si—OH silanol groups or the SiO$^-$ anionic groups at the silica surface. The organic agent can be added to the silica in the form of slurry before or after salts are removed, or can be sprayed on to dry silica.

A number of patent publications describe processes for making composite synthetic silica particles, including the following.

U.S. Pat. No. 2,731,326 describes a process of preparing xerogels in which a silica gel is stabilized so that the pores of the gel do not collapse upon drying. It involves a two-stage precipitation process where in the first stage silica gel is formed, and in the second stage a layer of dense amorphous silica is formed over the gel particles in order to provide sufficient reinforcement such that the pores do not collapse upon drying. The gel particles have a particle size in the range of 5 to 150 millimicrons (nm), and preferably have an average diameter of from 5 to 50 millimicrons. The resulting reticulated particles can be dewatered and dried into powder form. The '326 patent states that when silica particles have a specific surface area of greater than 200 $m^2/g$, it is preferred to replace the water with an organic liquid, and then dehydrate the silica particles. The '326 patent describes silica products with preferred specific surface areas 60 to 400 $m^2/g$. The '326 patent indicates little advantage is obtained in carrying the process of accretion to an extreme. The preferred products of the '326 patent process of accretion are limited so that the original dense ultimate units of the aggregates do not lose their identity and the original aggregates structure is not obscured.

U.S. Pat. No. 2,885,366 describes a process used to deposit a dense layer of silica over particles other than silica.

U.S. Pat. No. 2,601,235 describes a process for producing built-up silica particles in which a silica sol heel is heated above 60° C. to make nuclei of high molecular weight silica. The nuclei is mixed with an aqueous dispersion of active silica made by acidulating alkali metal silicate, and the mixture is heated above 60° C. at a pH of 8.7 to 10, such that active silica accretes to the nuclei.

U.S. Pat. No. 5,968,470 describes a process to synthesize silica having controlled porosity. It involves the addition of silicate and acid to a solution of colloidal silica with or without an electrolyte added (salt). The porosity can be controlled based upon the amount of colloidal silica added in the first step of the reaction. Silica with BET surface areas ranging from 20 to 300 $m^2/g$, CTAB specific surface areas from 10 to 200 $m^2/g$, oil absorption (DBP) ranging from 80 to 400 $m^2/g$, pore volumes from 1 to 10 $cm^3/g$, and mean pore diameters from 10 to 50 nm could be synthesized. The intended use of materials produced by this process is in the paper and catalysis marketplace.

U.S. Pat. No. 6,159,277 describes a process for the formation of silica particles with a double structure of a core of dense amorphous silica and a shell of bulky amorphous silica. A gel is formed in a first step. The gel is then aged, wet pulverized, and then sodium silicate is added in the presence of an alkali metal salt in order to form amorphous silica particles on the surface of the milled gel particles. The resultant double structure silica material has an average particle diameter of 2 to 5 micrometers and a surface area of 150 to 400 m²/g. The resultant material is said to have improved properties for use in as a delustering agent in paint and coatings.

Patent publications that describe use of silicas in dentifrice or oral cleaning compositions include the following.

U.S. Pat. No. 5,744,114 describes silica particles adopted for formulation into dentifrice compositions having a unique surface chemistry as to be at least 50% compatible with zinc values, and have a number of OH functions, expressed as $OH/nm^2$, of at most 15 and a zero charge point of from 3 to 6.5. The '114 patent describes a process of preparing silica particles by the reaction of silicate with an acid to form a suspension or gel of silica. The gel/suspension is then separated, washed with water and treated with acid to adjust the pH below 7.

U.S. Pat. No. 5,616,316 describes silica that is more compatible with customary dentifrice ingredients. In addition to many other ingredients, cationic amines are mentioned.

Another problem associated with usage of conventional silicas in dentifrices is that they often have flavor compatibility problems. That is, the conventional silicas tend to interact with flavorants included in the same dentifrice in a manner that creates off-flavors, making the product less palatable. This off-flavor problem accompanying use of some conventional silicas in dentifrices is highly undesirable from a consumer satisfaction standpoint.

A need exists for silicas that can be used together with anti-microbial agents such as CPC in oral cleaning compositions such as dentifrices without impairing the respective functions of either ingredient. Silicas that are more flavor compatible are also in need. In general, the silica disclosed in this invention may be useful whenever it is desirable to limit the interaction of the silica particulate with desirable additives and components found in dentifrice formulations. The present invention meets these needs and others as will become readily apparent from the disclosure that follows.

SUMMARY OF THE INVENTION

This invention relates to a unique silica product comprising silica particles that have been surface-modified in a beneficial manner. This silica product is particularly useful in dentifrice compositions containing cetylpyridinium chloride ("CPC") or other therapeutic agents. CPC does not appreciably bind to these silica products. Therefore, when contained in a dentifrice composition, an increased amount of CPC remains available for its antimicrobial duties while the silica abrasive remains unimpaired by CPC attachment, and it is able to provide the mechanical cleaning and polishing action desired from it as an abrasive silica product. Additionally, the silica product is highly compatible with many commonplace dentifrice flavorants. The silica product of embodiments of this invention reduce the possibility of off-flavors when present together with flavorants. Also, the silica product is highly compatible with fluoride ion sources such as sodium fluoride. The silica product does not adversely interact with or impair those anticaries agents or their function.

The silica product of embodiments of this invention may be produced via a process including steps of providing porous silica substrate particles as a pre-formed material or forming it in-situ, followed by precipitating active silica upon the silica substrate particles effective to satisfy the pore size distribution requirements described herein. In one embodiment, a dense silica material is deposited on the silica substrate particles effective to penetrate into and/or block at least part of the pore openings on the silica substrate particles to reduce the pores having a size greater than about 500 Å effective to limit the cumulative surface area for those sized pores on the surface-treated silicas to less than approximately 8 m²/g, as measured by mercury intrusion porosimetry. Experimental results reported herein reveal that pores sized greater than about 500 Å are more accessible to CPC intrusion than pores having smaller sizes. Consequently, it has been discovered that the reduction of pores on the silica particles having sizes of greater than about 500 Å is essential to limit CPC intrusion and thus CPC loss to pores at the surfaces of the silica particles. For instance, where CPC and silica are slurried in a common aqueous solution, the CPC is apt to intrude into silica surface pores having sizes of greater than about 500 Å, but with much more difficulty into smaller pore sizes. Therefore, it has been discovered that filling pores on the silica particles having sizes of greater than about 500 Å provides silicas that are significantly more compatible with CPC.

Precipitated silica products prepared according to embodiments of this invention so as to reduce the cumulative surface area of all pores having sizes greater than about 500 Å to less than approximately 8 m²/g, generally have a % CPC Compatibility value of at least 55%, particularly greater than 60%, and more particularly greater than 70%, and even more particularly greater than 80%, and it generally ranges between about 55% to about 95%. The "% CPC Compatibility" value of a silica is determined by a testing procedure explained in the more detailed descriptions provided below. These % CPC Compatibility values are attainable due to the treatment of the silica substrate particles effective to reduce the surface pores having a size greater than about 500 Å such that the cumulative surface area of those sized pores generally is less than approximately 8 m²/g, and preferably less than approximately 7 m²/g, and more preferably less than approximately 6 m²/g, as measured by mercury intrusion porosimetry.

Dentifrices that contain this silica product offer the benefit that CPC also can be used which remains at an effective antibacterial level in the dentifrice despite the co-presence of silica abrasive. As another benefit and advantage, dentifrices containing the silica product have superior flavor attributes. The flavor compatibility of the silica product of this invention is superior to current commercial dental-grade silica materials.

The oral cleaning compositions that can be benefited by incorporation of the silica product of embodiments of this invention include, for example, dentifrices, chewing gums, and mouthwashes, and the like. The term "dentifrice" means oral care products in general such as, without intending to be limited, toothpastes, tooth powders, and denture creams. The silica particles of embodiments of the invention also have wider cleaning utility and application, including, for instance, as a metal, ceramic or porcelain cleaning or scrubbing agent.

For purposes herein, the terminology "silica particles" means finely divided silica, and the term encompasses silica primary particles, silica aggregates (i.e., unitary clusters of a plurality of silica primary particles), silica agglomerates (i.e., unitary clusters of a plurality of silica aggregates), singly or in combinations thereof. The term "denser", as used in herein, refers to a lower porosity silica particulate.

DETAILED DESCRIPTION OF THE PREFERRED EMBODIMENTS

Figure 1:
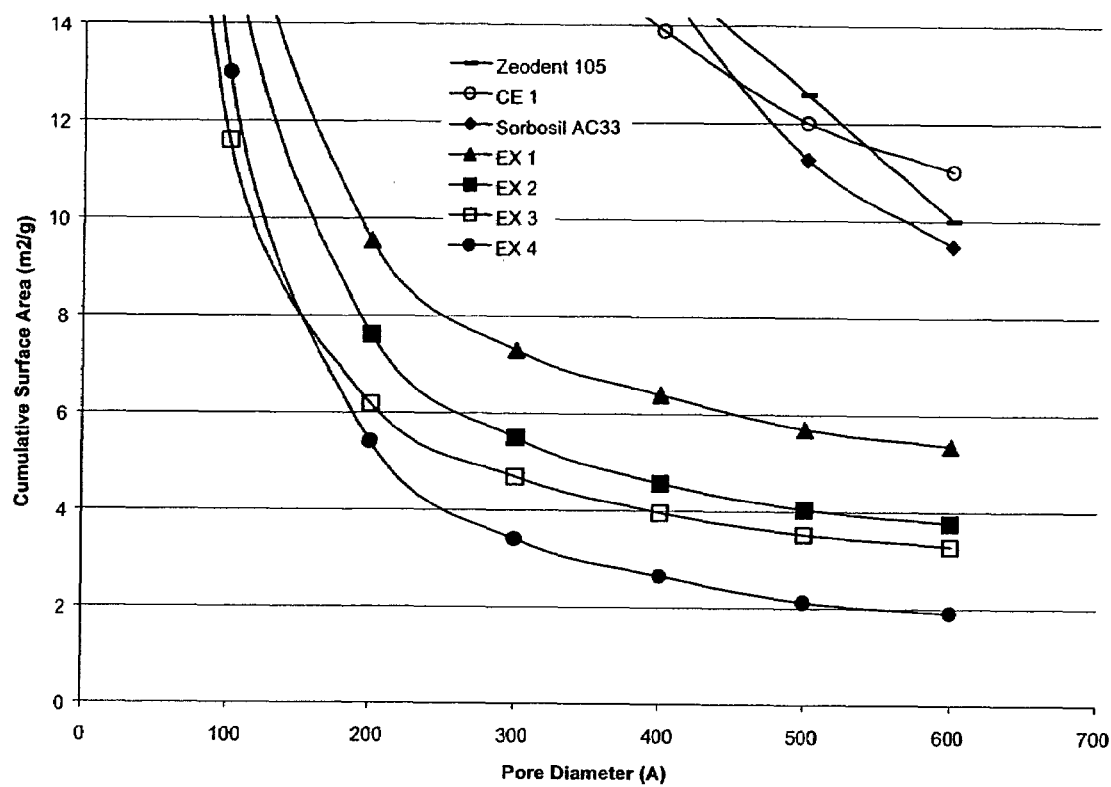
FIG. 1 is a plot of cumulative surface area (m²/g) measured at various pore sizes for a series of silicas representing embodiments of this invention and also comparison silicas represented by commercial silicas determined as described in examples herein.

In accordance with the preceding summary, the present invention is directed to a unique silica product, which is particularly useful in dentifrice compositions containing therapeutic agents, such as CPC. The silica product of embodiments of the present invention limits the ability of CPC to bind to these products. Consequently, loss of CPC due to inadvertent interaction with silica abrasive particles is minimized.

The silica product of an embodiment of this invention may be produced by a general process scheme, in which:
1) a slurry of amorphous silica particles is provided either by slurrying up a prefabricated silica material obtained in dry finely divided form, or, alternatively, from an ongoing production run in which fresh precipitated silica is in slurry or wet cake form without ever having been dried into powder form, followed by;
2) precipitating active silica upon the substrate silica particles effective to reduce the cumulative surface area of all pores having sizes greater than about 500 Å to less than approximately 8 $m^2/g$, and preferably less than approximately 7 $m^2/g$, and more preferably less than approximately 6 $m^2/g$, as measured by mercury intrusion porosimetry. The % CPC Compatibility values of such surface-modified silica products is at least 55%, particularly greater than 60%, and more particularly greater than 70%, and even more particularly greater than 80%, and generally ranges between about 55% to 95%.

It has been discovered that CPC compatibility, as measured according to the technique set forth herein, is not related to the overall surface area of the silica, but, instead, it is directly related to the cumulative surface area of the pores having sizes greater than approximately 500 Å. In general, the greater the reduction of pores having sizes greater than approximately 500 Å in a silica product, the better the % CPC compatibility attained. Reducing the presence of pore sizes less than about 500 Å does not significantly influence the CPC compatibility achieved.

For purposes of measuring BET surface area, $N_2$ physisorption is commonly used. However, because of the size of nitrogen gas, there are pores contributing to the overall surface area on silica particles that are accessible to the gaseous $N_2$ used in conventional BET measurements, but which are not readily accessible to CPC. That is, surface area resulting from micropores may be accessible to gaseous nitrogen (as measured by $N_2$ physisorption), but is not readily accessible to an aqueous slurry of CPC in the time used to measure CPC compatibility as described herein. Consequently, it is not possible to use BET surface area measurements per se to identify silica particles having the favorable pore size distributions described herein for obtaining % CPC Compatibility values of greater than approximately 55%. Instead, mercury intrusion porosimetery is used in embodiments of the present invention as the method for measuring cumulative surface area of the silica particles at the identified critical pore size values.

As generally known, the mercury porosimetry technique is based on the intrusion of mercury into a porous structure under stringently controlled pressures. From the pressure versus intrusion data, the instrument generates volume and size distributions using the Washburn equation. Since mercury does not wet most substances and will not spontaneously penetrate pores by capillary action, it must be forced into the pores by the application of external pressure. The required pressure is inversely proportional to the size of the pores, and only slight pressure is required to intrude mercury into large macropores whereas much greater pressures are required to force mercury into micropores. Higher pressures are required to measure the pore sizes and surface areas of the micropores present on the surfaces of silica products of the present invention. Suitable instruments for measuring micropore sizes and surface areas using mercury intrusion porosimetry for purposes of the present invention is a Micromeritics® Autopore II 9220 series automated mercury porosimeters, and the like.

Sourcing of Silica Substrate Particles

Regarding the silica particles provision of above general step 1), amorphous silica particles are provided. If provided in dry form, the dried crude silica used as the "particles" to be surface-modified according to this invention includes commercially obtainable precipitated silicas, such as Zeodent® 113, Zeodent® 115, Zeodent® 153, Zeodent® 165, Zeodent® 623, Zeodent® 124 silicas, and so forth, which are available from J.M. Huber Corporation. These commercially available silicas typically are in aggregate form.

The dry finely divided silica particles also may be obtained from a supply of premanufactured material made earlier at the same or different production facility where procedures used for the surface area reduction step can be performed at a later time.

The dry precipitated silicas to be used as the substrate particles for the surface area reduction operation generally should have a median particle size of 1 to 100 μm, a BET specific surface area value of approximately 30 to 100 $m^2/g$, and a linseed oil absorption of approximately 40 to 250 ml/100 g. Zeodent® 113, for example, typically has a median particle size of approximately 10 μm, BET surface area value of approximately 80 $m^2/g$, and a linseed oil absorption of approximately 85 ml/100 g. The silica particles used as the substrate material for the coating operation, described below, preferably are constituted of silica particles having a median diameter of 1 to 100 micrometers. Substrate materials, such as high structure precipitated silica, silica gels and pyrogenic silica, with BET surface area greater than 100 $m^2/g$, such as about 100 to 800 $m^2/g$, or linseed oil absorption greater than 120 ml/100 g, such as about 120 to 400 ml/100 g, can be used in the present invention, although longer surface area reduction times (active silica deposition times) will be required to lower the surface area to desired levels.

The dry precipitated silicas must be slurried in an aqueous medium before they can be subjected to the dense silica coating application procedure described herein. Generally, the dry silicas are slurried to a solids content that creates a pumpable mixture, generally of from about 1 to about 50%.

Alternatively, crude undried liquid phase silica materials can be prepared in situ during a common production run scheme as the surface area reduction operation. Alternatively, a crude silica wet cake can be stored for later slurrying, or stored as a slurry thereof, until the surface area reduction procedure is performed at a subsequent time, without ever drying the silica solids to powder form. The solids content of the slurry provided before the surface area reduction operation is performed will be the same as that described above in connection with the dry silicas.

The liquid phase source of precipitated silicas generally should have constituent particle sizes, overall particle size, BET specific surface area value, and linseed oil absorption properties comparable to those respective values described above in connection with the dry source form of the silica. To the extent they meet those physical criteria, the liquid phase silicas can include amorphous precipitated silicas, silica gels or hydrogels, pyrogenic silica and colloidal silicas. In one aspect, the silica particles provided in situ are in aggregate or agglomerate form.

The silicas can be produced by acidulating an alkali metal silicate with a mineral acid, such as sulfuric acid, or organic acid, with heating. Synthetic amorphous precipitated silicas are generally prepared by admixing alkaline silicate solutions with acids with heating, stirring, and then filtering or centrifuging to isolate the precipitated silica solids as a wet cake form thereof. The reaction media may optionally contain an electrolyte, such as sodium sulfate. Wet cake of silica generally contains about 40 wt % to about 60 wt % water, and the remainder is principally solids. The precipitated reaction mass generally is filtered and washed with water to reduce the $Na_2SO_4$ levels to tolerable levels. Washing of the reaction product is generally conducted after filtering. The pH of the washed wet cake can be adjusted, if necessary, prior to proceeding to subsequent steps described herein. If necessary, the washed wet cake is slurried to a solids content of between 1 to 50% before the surface area reduction procedure is performed on it. As previously noted, if the silica is dried, or dried and comminuted to a desired size, it must be reslurried before the surface area reduction procedure can be conducted on the crude silica.

To the extent they meet other requirements discussed herein, the crude silica to be used as a source of the substrate particles for particular type of surface area reduction described herein can be, for example, precipitated silicas made as described in U.S. Pat. Nos. 4,122,161, 5,279,815 and 5,676,932 to Wason et al., and U.S. Pat. Nos. 5,869,028 and 5,981,421 to McGill et al., which teachings are incorporated herein by reference.

Surface Area Reduction of Silica Substrate Particles

Regarding the surface area reduction of above general step 2) for pore sizes larger than about 500 Å, after slurrying the crude silica particles in an aqueous medium, active silica is generated in the same medium for a time period and under conditions sufficient to provide dense amorphous silica deposits on the substrate particles sufficient to reduce the surface area and CPC's potential for binding to it. In general, the slurried crude silica particle intermediate product is dispersed in an aqueous medium in which active silica is generated by acidulating an alkali metal silicate with a mineral acid therein. The resulting mixture is gently agitated or mixed, such as with a paddle mixer, for a sufficient period of time to ensure that the active silica and substrate silica particles are substantially uniformly dispersed. The resulting silica product is filtered or otherwise dewatered, washed, and dried as needed.

In this regard, the methodology used to provide the active silica in the medium that is deposited as an amorphous silica material on the surfaces of the substrate particles generally involves similar chemistries and conditions applied to make the crude or substrate particles, except that the addition rates of the silicate and acid used for formation of active silica must be sufficiently slowed in order to insure the active silica deposits on the existing substrate silica particles and does not form separate precipitated particles. The addition of active silica too rapidly will result in the formation of separate precipitated silica particles and will not result in the desired decrease in surface area of the substrate silica. It is desirable to use temperatures ranging from 60 to 100° C., pH from 7 to 10, and an active silica deposition rate such that the specific surface area of the of the silica particles material is reduced. Optionally, a salt such as $Na_2SO_4$ can be added in an amount such that the desired decrease in surface area is still obtained. Reaction temperatures of greater than 90° C. and pH greater than 9 are preferred for use during the surface area reduction portion of the process.

In one aspect, the surface area reduction process is manipulated appropriately to ensure that the extent of deposition of active silica is at a rate and in an amount effective to provide a surface area, as measured by mercury intrusion, for pore sizes large than about 500 Å of less than about 8 square meters per gram, preferably less than about 7 square meters per gram, more preferably less than about 6 square meters per gram. It also should be in amount effective to reduce binding of CPC thereto as compared to the silica particles that has not been exposed to a surface area reduction process.

The precipitated silica product has a % CPC Compatibility value generally of at least about 55%, particularly greater than 60%, more particularly greater than 70%, and can be even greater than 80%. The % CPC Compatibility value generally can range between about 55% to about 95%. The "% CPC Compatibility" characteristic of the silica is determined by a testing procedure explained in the examples that follow.

The resulting silica also generally has a median particle size ranging between about 1 to about 100 microns, and preferably in one embodiment ranges between about 5 and about 20 microns. The particle size of the silicas is measured using a Horiba Particle Analyzer. Model LA-910 manufactured by Horiba Instruments, Boothwyn, Pa.

The resulting silica product can be spray dried in a similar manner as the treatment performed on the crude freshly prepared silicas. Alternatively, the wet cake obtained can be reslurried, and handled and supplied in slurry form or supplied as a filter cake, directly.

Also, drying of silicas described herein can be effected by any conventional equipment used for drying silica, e.g., spray drying, nozzle drying (e.g., tower or fountain), flash drying, rotary wheel drying or oven/fluid bed drying. The dried silica product generally should have a 1 to 15 wt. % moisture level. The nature of the silica reaction product and the drying process both are known to affect the bulk density and liquid carrying capacity. Further, care must be taken that the drying operation and subsequent operations do not detrimentally affect the structure of the silica obtained in the precipitation stage. The dried silica product is in a finely divided form. In one particular embodiment, the water content of the precipitated silica-containing fractions is about 25% by weight or more for all times until the drying procedure is performed on the silica product.

To decrease the size of the dried silica particles further, if desired, conventional grinding and milling equipment can be used. A hammer or pendulum mill may be used in one or multiple passes for comminuting and fine grinding can be performed by fluid energy or air-jet mill. Products ground to the desired size may be separated from other sizes by conventional separation techniques, e.g., cyclones, classifiers or vibrating screens of appropriate mesh sizing, and so forth.

There are also ways to reduce the particle size of the resulting silica product before isolation and/or during the synthesis of the silica product that affect the size of the dried product or product in slurry form. These include but are not limited to media milling, the use of high shear equipment (e.g. high shear pump or rotor-stator mixers), or ultrasound devices. Particle size reduction carried out on the wet silica product can be done at anytime before drying, but more preferably during formation of the core and/or the deposition of the active silica onto the core. Any particle size reduction done on the dry or wet silica product should be done in a way not to significantly reduce the CPC compatibility of the final product.

The recovery of the dried silica in the present invention does not require silica dewatering and dehydration to be performed with an organic solvent replacement procedure. The isolation of the silica product can be performed from an aqueous medium without occurrence of product degradation.

Dentifrice Compositions

Dentifrices that contain the above-described silica product offer the benefit that therapeutic agents, such as CPC also can be used which remains at an effective antibacterial level in the dentifrice despite the presence of silica abrasive. The silica particles show decreased interaction with CPC and as a result there remains an increase in the free CPC in the dentifrice available to improve antibacterial efficacy.

While CPC is used herein as representative of dentifrice therapeutic agents, other antimicrobial agents, (cationic, anionic and nonionic) are contemplated by the invention. Other suitable antimicrobial agents include bisguanides, such as alexidine, chlorhexidine and chlorhexidine gluconate; quarternary ammonium compounds, such as benzalkonium chloride (BZK), benzethonium chloride (BZT), cetylpyridinium chloride (CPC), and Domiphen bromide; metal salts, such as zinc citrate zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination.

As another benefit and advantage, dentifrices containing the silica product have a superior flavor attributes. Dentifrice compositions incorporating the silica product described herein generally contain the silica in an effective amount for abrasive and polishing action. This amount can vary, depending on other ingredients of the formulation, for example, but generally will range from about 5 to about 60 wt %.

Dentifrice compositions incorporating the silica product described herein preferably also contain CPC in an antimicrobial effective amount. This amount can vary, depending on other ingredients of the formulation and limitations placed upon its use by regulating authorities (e.g. FDA), for example, but generally will range from about 0.01 to about 1 wt %., preferably from about 0.1 to about 0.75 wt. %, most preferably from about 0.25 to 0.50 wt. %.

Other additives commonly used or otherwise beneficial in dentifrices also optionally may be included in the formulation. A pharmaceutically acceptable carrier for the components of dentifrice compositions containing the silica product of the present invention is optional and can be any dentifrice vehicle suitable for use in the oral cavity. Such carriers include the usual components of toothpastes, tooth powders, prophylaxis pastes, lozenges, gums, and the like and are more fully described thereafter.

Flavoring agents optionally can be added to dentifrice compositions. Suitable flavoring agents include oil of Wintergreen, oil of peppermint, oil of spearmint, oil of sassafras, and oil of clove, cinnamon, anethole, menthol, and other such flavor compounds to add fruit notes, spice notes, etc. These flavoring agents consist chemically of mixtures of aldehydes, ketones, esters, phenols, acids, and aliphatic, aromatic and other alcohols.

Sweetening agents, which can be used, include aspartame, acesulfame, saccharin, dextrose, levulose and sodium cyclamate. Flavoring and sweetening agents are generally used in dentifrices at levels of from about 0.005% to about 2% by weight A water-soluble fluoride compound optionally can be added and present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. Nos. 3,535,421, and 3,678,154, both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes and dentifrices according to another embodiment of this invention. Water employed in the preparation of suitable toothpastes should preferably be deionized and free of organic impurities. Water generally comprises from about 2% to 50%, preferably from about 5% to 20%, by weight, of the toothpaste compositions. These amounts of water include the free water which is added plus that which is introduced with other additives and materials, such as humectant.

In preparing toothpastes, it often is necessary to add some thickening or binder material to provide a desirable consistency and thixotropy. Preferred thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Thickening agents in an amount from about 0.5% to about 5.0% by weight of the total composition generally can be used.

Silica thickeners can also be used to modify toothpaste rheology. Precipitated silica, silica gels and fumed silica can be used. Silica thickeners can be added generally at a level of about 5% to about 15%.

It is also often desirable to include some humectant material in a toothpaste to keep it from hardening. Suitable humectants include glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. Suitable humectants can be added generally at a level of from about 15% to about 70%.

Chelating agents optionally can be added to the dentifrices of the invention, such as alkali metal salts of tartaric acid and citric acid, or alkali metal salts of pyrophosphates or polyphosphates.

Other optional ingredients and adjuvants of dentifrices, such as those described in U.S. Pat. No. 5,676,932 and Pader, M., Oral Hygiene Products and Practice, Marcel Dekker, Inc., New York, 1988, for instance, also can be added as needed or desired. These other optional adjuvants, additives, and materials that can be added to the dentifrice compositions of the present invention include, for example, foaming agents (e.g., sodium lauryl sulfate), detergents or surfactants, coloring or whitening agents (e.g., titanium dioxide, FD&C dyes), preservatives (e.g., sodium benzoate, methyl paraben), chelating agents, antimicrobial agents, and other materials that can be used in dentifrice compositions.

The optional additives, if present, generally are present in small amounts, such as no greater than about 6% by weight each.

In all cases, the ingredients used in dentifrice formulations, such as thickening gums, foaming agents, etc., are selected to be compatible with the therapeutic agents and flavors.

Additionally, while the usefulness of the abrasive cleaning material of this invention is specifically illustrated in oral cleaning compositions, it is will be appreciated that the silica of this invention has wider usefulness. For instance, it can be used in metal, ceramic or porcelain cleaning or scrubbing and as a CMP (Chemical Mechanical Planarization) polishing agent.

EXAMPLES

The following examples are presented to illustrate the invention, but the invention is not to be considered as limited thereto. In the following examples, parts are by weight unless indicated otherwise.

In the following examples, a series of silica products were prepared with varied surface treatments to investigate possible relationships between cumulative surface areas provided for various pore size values and the CPC compatibility attained for the silica products. Several commercially available silica products also were analyzed for sake of comparison.

Preparation of Silica Substrate Particles

For the following Examples 1-3 and Comparative Examples 1-2, the silica substrates used were portions of a bead-milled silica wet cake that was prepared in the following manner.

1900 liters of sodium silicate solution (13%, 2.50 M.R.) was added to a stainless steel reactor and was heated to 85° C. with stirring. Sodium silicate (13%, 2.50 molar ratio (M.R.)) and sulfuric acid (11.4%) were simultaneously added to the reactor at rates of 387.5 and 170.3 LPM, respectively, for 48 minutes. After 48 minutes, the flow of silicate to the reactor was stopped and the pH was adjusted to 5.0 to 5.2 with the continued addition of sulfuric acid (11.4%). The reaction mixture was then digested for 10 minutes at 93° C. Silica wet cake was recovered from the reaction mixture.

The silica wetcake was bead milled in the following manner. A Cobal® Mill MS-50 Machine # 74996/00 manufactured by Romaco AG, Frymakoruma, was used for the bead mill processing. 7 liters of 2.0-2.5 mm Zirconium Oxide beads by SEPR were used as the charge for milling media. The silica wetcake was diluted with water to provide a pumpable slurry (31.8% solids) which was fed at a rate 2.0 liters per minute to the Cobal® Mill. The silica slurry was bead milled to a top particle size of approximately 35 μm.

Preparation of Surface-Coated Silica Particles

Example 1

63 L of bead milled silica substrate particles (~33.55 % solids) were added to a 400 gallon reactor along with 265 L of water. The slurry was heated to 95° C. with stirring at 78 RPM. Once a temperature of 95° C. was reached, sodium silicate (13.3%, 2.65 M.R. pre-heated to 90° C., 1.123 g/ml S.G.) was added at 3.6 L/min until pH 9.5 was reached. Once a pH of 9.5 was reached, sulfuric acid (11.4%) was added at ~1.9 L/min in order to maintain this pH. If necessary, the acid flow rate was adjusted to maintain pH 9.5. After 150 minutes, the silicate flow was stopped and the pH was adjusted to 5.0 with the addition of sulfuric acid at 3.8 L/min. Once a pH of 5.0 was reached, the flow of acid was stopped and this pH was maintained for a period of 10 minutes. The reaction mixture was then filtered, washed with water until a conductivity of <1500 μS, and then spray dried.

Example 2

43 L of bead milled silica substrate particles (~33.55 % solids) were added to a 400 gallon reactor along with 180 L of water. The slurry was heated to 95° C. with stirring at 78 RPM. Once a temperature of 95° C. was reached, sodium silicate (13.3%, 2.65 M.R., pre-heated to 90° C., 1.123 g/ml S.G.) was added at 4.7 L/min until a pH of 9.5 was reached. Once a pH of 9.5 was reached, sulfuric acid (11.4%) was added at ~2.2 L/min in order to maintain this pH. If necessary, the acid flow rate was adjusted to maintain a pH of 9.5. After 30 minutes the flow of silicate was adjusted to 4.5 L/min and the flow of acid to ~2.2 L/min. After 60 minutes the flow of silicate was adjusted to 4.2 L/min and the flow of acid to ~2.0 L/min. After 90 minutes the flow of silicate was adjusted to 3.6 L/min and the flow of acid to ~1.7 L/min. After 120 minutes the flow of silicate was adjusted to 3.1 L/min and the flow of acid to ~1.5 L/min. After 150 minutes, the silicate flow was stopped and the pH was adjusted to 5.0 with the addition of sulfuric acid at 3.8 L/min. Once pH 5.0 was reached, the flow of acid was stopped and this pH was maintained for a period of 10 minutes. The reaction mixture was then filtered, washed with water until a conductivity of <1500 μS, and then spray dried.

Example 3

33 L of bead milled silica substrate particles (~33.55% solids) were added to a 400 gallon reactor along with 138 L of water. The slurry was heated to 95° C. with stirring at 78 RPM. Once a temperature of 95° C. was reached, sodium silicate (13.3%, 2.65 M.R., pre-heated to 90° C., 1.123 g/ml S.G.) was added at 5.1 L/min until a pH of 9.5 was reached. Once a pH of 9.5 was reached, sulfuric acid (11.4%) was added at ~2.4 L/min in order to maintain this pH. If necessary, the acid flow rate was adjusted to maintain a pH of 9.5. After 30 minutes the flow of silicate was adjusted to 4.9 L/min and the flow of acid to ~2.3 L/min. After 60 minutes the flow of silicate was adjusted to 4.5 L/min and the flow of acid to ~2.2 L/min. After 90 minutes the flow of silicate was adjusted to 4.0 L/min and the flow of acid to ~1.9 L/min. After 120 minutes the flow of silicate was adjusted to 3.5 L/min and the flow of acid to ~1.7 L/min. After 150 minutes, the silicate flow was stopped and the pH was adjusted to 5.0 with the addition of sulfuric acid at 3.8 L/min. Once pH 5.0 was reached, the flow of acid was stopped and this pH was maintained for a period of 10 minutes. The reaction mixture was then filtered, washed with water until a conductivity of <1500 μS, and then spray dried.

Comparative Example 1

113 L of bead milled silica substrate particles (~33.55% solids) were added to a 400 gallon reactor along with 460 L of water. The slurry was heated to 95° C. with stirring at 78 RPM. Once a temperature of 95° C. was reached, sodium silicate (13.3%, 2.65 M.R., pre-heated to 90° C., 1.123 g/ml S.G.) was added at 2.4 L/min until pH 9.5 was reached. Once a pH of 9.5 was reached, sulfuric acid (11.4%) was added at ~1.3 L/min in order to maintain this pH. If necessary, the acid flow rate was adjusted to maintain a pH of 9.5. After 150 minutes, the silicate flow was stopped and the pH was adjusted to 5.0 with the addition of sulfuric acid at 3.8 L/min. Once a pH of 5.0 was reached, the flow of acid was stopped and this pH was maintained for a period of 10 minutes. The reaction mixture was then filtered, washed with water until a conductivity of <1500 µS, and then spray dried.

Comparative Example 2

90 L of bead milled silica substrate particles (~33.55% solids) were added to a 400 gallon reactor along with 360 L of water. The reaction mixture was heated to 95° C. with stirring at 78 RPM. Once a temperature of 95° C. was reached, sodium silicate (13.3%, 2.65 M.R., pre-heated to 90° C., 1.123 g/ml S.G.) was added at 3.3 L/min until a pH of 9.5 was reached. Once a pH of 9.5 was reached, sulfuric acid (11.4%) was added at 1.7 L/min in order to maintain this pH. If necessary, the acid flow rate was adjusted to maintain a pH of 9.5. After 150 minutes, the silicate flow was stopped and the pH was adjusted to 5.0 with the addition of sulfuric acid at 3.8 L/min. Once pH 5.0 was reached, the flow of acid was stopped and this pH was maintained for a period of 10 minutes. The reaction mixture was then filtered, washed with water until a conductivity of <1500 µS, and then spray dried.

For Examples 1-3 and Comparative Examples 1-2, as well as any other examples summarized herein, the "% CPC Compatibility" value was determined in the following manner.

"% CPC Compatibility" Test 27.00 g of a 0.3% solution of CPC was added to a 3.00 g sample of the silica to be tested. The silica was previously dried at 105° C. to 150° C. to a moisture content of 2% or less, and the pH of the sample was measured to ensure the 5% pH was between 5.5 and 7.5. The mixture was shaken for a period of 10 minutes. Accelerated aging testing requires agitation of the test specimen for 1 week at 140° C. After agitation was complete, the sample was centrifuged and 5 ml of the supernatant was passed through a 0.45 µm PTFE milli-pore filter and discarded. An additional 2.00 g of supernatant was then passed through the same 0.45 µm PTFE milli-pore filter and then added to a vial containing 38.00 g of distilled water. After mixing, an aliquot of the sample was placed in a cuvette (methyl methacrylate) and the U.V. absorbance was measured at 268 nm. Water was used as a blank. The % CPC Compatibility was determined by expressing as a percentage the absorbance of the sample to that of a CPC standard solution prepared by this procedure with the exception that no silica was added.

% Active Silica Deposited

A "% Active Silica Deposited" was determined for silica products by calculation from the batch parameters. Active silica is determined by knowing the volume of active silica used and the silicate concentration, specific gravity (S.G.) and molar ratio (M.R.). Likewise, the total batch silica is calculated by knowing the total volume of silica used and silicate concentration, S.G. and M.R. % active silica deposited equals g active silica divided by g total batch silica times 100. All terms except the volumes cancel so that the % active silica deposited equals the active silica volume/total silica volume. When starting with a premanufactured silica substrate, which is measured in weight values, one must use the above equation to convert active silica to a weight measure, such as grams to put all ingredients on the same basis.

Table 1 below is a summary of the CPC compatibility and % active silica deposited for the silicas produced in the preceding examples and comparison examples.

TABLE 1

| Sample | % Active Silica Deposited | % CPC Compatibility |
|---|---|---|
| CE1 | 45 | 14.7 |
| CE2 | 60 | 43.9 |
| 1 | 70 | 66.7 |
| 2 | 80 | 76.6 |
| 3 | 85 | 76.8 |

In Table 2 below, a summary of the physical properties of the CPC compatible silica samples produced by the preceding examples is set forth. Median particle size was measured using a Microtrac II apparatus, made by Leeds and Northrup. The BET and linseed oil absorption properties were measured in the respective manners described in commonly assigned U.S. Pat. No. 5,981,421, which descriptions are incorporated herein by reference. The % 5 pH values of the silicas (i.e., a 5 weight % silica slurry) were measured by a conventional pH sensitive electrode. CTAB external surface area of silica is determined by absorption of CTAB (cetyltrimethylammonium bromide) on the silica surface, the excess separated by centrifugation and determined by titration with sodium lauryl sulfate using a surfactant electrode. The external surface of the silica is determined from the quantity of CTAB adsorbed (analysis of CTAB before and after adsorption). Specifically, about 0.5 g of silica is placed in a 250-ml beaker with 100.00 ml CTAB solution (5.5 g/L), mixed on an electric stir plate for 1 hour, then centrifuged for 30 minutes at 10,000 rpm. One ml of 10% Triton X-100 is added to 5 ml of the clear supernatant in a 100-ml beaker. The pH is adjusted to 3.0-3.5 with 0.1 $\underline{N}$ HCl and the specimen is titrated with 0.0100 M sodium lauryl sulfate using a surfactant electrode (Brinkmann SUR1501-DL) to determine the endpoint.

TABLE 2

| Sample | CTAB ($m^2/g$) | BET ($m^2/g$) | Oil Absorption (cc/100 g) | 5% pH | Median particle size (µm) |
|---|---|---|---|---|---|
| CE1 | 10 | 24 | 78 | 7.36 | 3.8 |
| CE2 | 7 | 19 | 90 | 6.68 | 5.1 |
| 1 | 3 | 2 | 78 | 6.82 | 5.9 |
| 2 | 1 | 6 | 58 | 6.79 | 6.7 |
| 3 | 1 | 9 | 58 | 6.27 | 7.0 |

Example 4

In this example, the silica was precipitated, and comminuted, at the reaction vessel in the following manner. 40 L of sodium silicate (13%, 3.32 M.R., 1.112 g/ml S.G.) was added to a 400-gallon reactor and was heated to 95° C. with stirring at 50 RPM. Once the temperature stabilized at 95° C., a Silverson in-line mixer coupled to the reactor by a re-circulation line was set to 100 Hz with re-circulation of 100 Hz. Sodium silicate (13%, 3.32 M.R., pre-heated to 90° C., 1.112 g/ml S.G.) and sulfuric acid (11.4%) were then simultaneously added to the reactor at rates of 7.8 L/min and 2.3 L/min, respectively, for 47 minutes. After 15 minutes, the stir rate was increased to 75 RPM. After 47 minutes, the Silverson in-line mixer was stopped. Sodium silicate addition was adjusted to 2.2 L/min and the pH was adjusted to 9.5+/−0.2 with continued addition of sulfuric acid (11.4%). Once the pH reached 9.5, sulfuric acid (11.4%) was added a rate of ~0.7 L/min. If necessary, the acid rate was adjusted to maintain pH 9.5+/−0.2. After 197 minutes (total), the flow of sodium silicate was stopped and the pH was adjusted to 5.0 with the addition of sulfuric acid (11.4%) at 2.3 L/min. The batch was digested for 10 minutes at pH 5.0, was filtered, washed to conductivity <1500 μS, and spray dried. The silica product obtained had a % CPC Compatibility value of 81.5.

The silica product obtained also had the physical properties indicated in Table 3.

TABLE 3

| Sample | CTAB ($m^2/g$) | BET ($m^2/g$) | Oil (ml/100 g) | % H2O | 5% pH | Median Particle Size (μm) |
|---|---|---|---|---|---|---|
| 4 | 7 | 11 | 28 | 5.46 | 7.12 | 12.7 |

For comparison purposes, the physical properties were measured on a commercial silica product sold as Sorbosil AC33 by INEOS, which are summarized in Table 4.

TABLE 4

| Sample | CTAB ($m^2/g$) | BET ($m^2/g$) | % CPC Compatibility |
|---|---|---|---|
| Sorbosil AC33 | 15 | 218 | 46.0 |

Characterization of Silica by Hg Intrusion Porosimetry

Hg intrusion porosimetry analyses was performed as follows on the silica samples prepared in these examples, and on comparative example 1 and several commercially available silicas including Sorbosil AC33 and Zeodent® 105.

The total pore volume (Hg) for these silica samples was measured at a series of different pore diameter ranges by mercury porosimetry using a Micromeritics Autopore II 9220 apparatus. The pore diameters can be calculated by the Washburn equation employing a contact angle Theta (θ) equal to 130° and a surface tension gamma equal to 484 dynes/cm. This instrument measures the void volume and pore size distribution of various materials. Mercury is forced into the voids as a function of pressure and the volume of the mercury intruded per gram of sample is calculated at each pressure setting. Total pore volume expressed herein represents the cumulative volume of mercury intruded at pressures from vacuum to 60,000 psi.

Increments in volume ($cm^3/g$) at each pressure setting are plotted against the pore radius or diameter corresponding to the pressure setting increments. The peak in the intruded volume versus pore radius or diameter curve corresponds to the mode in the pore size distribution and identifies the most common pore size in the sample. Specifically, sample size is adjusted to achieve a stem volume of 30-50% in a powder penetrometer with a 5 ml bulb and a stem volume of about 1.1 ml. Samples are evacuated to a pressure of 50 μm of Hg and held for 5 minutes. Mercury fills the pores from 1.5 to 60,000 psi with a 10 second equilibrium time at each of approximately 150 data collection points.

Hg intrusion porosimetry gave information about pores from approximately 100 Å to those over 1 μm in size. In comparison, $N_2$ physisorption (BET) gives information from pores approximately 5 to 1000 Å in size.

The cumulative pore area for different ranges of pore diameters is shown in the Table 5 below. Total cumulative pore area is the total pore area measured by mercury intrusion. Cumulative pore areas for the different ranges are described as the pore area from the specified pore size and up. For example, ">50 Å" means the cumulative pore area in $m^2/g$ for pores having an average pore diameter of 50 angstroms and greater.

TABLE 5

| | | | Cumulative Pore Area (m2/g) | | | | | | | |
|---|---|---|---|---|---|---|---|---|---|---|
| Sample | % CPC | Legend | Total | >50 Å | >100 Å | >200 Å | >300 Å | >400 Å | >500 Å | >600 Å |
| Example 1 | 66.7 | ▲ | 84.42 | 44.23 | 18.32 | 9.54 | 7.30 | 6.40 | 5.70 | 5.37 |
| Example 2 | 76.6 | ■ | 88.78 | 41.18 | 16.03 | 7.62 | 5.50 | 4.57 | 4.05 | 3.77 |
| Example 3 | 76.8 | □ | 55.81 | 27.72 | 11.60 | 6.19 | 4.69 | 3.97 | 3.53 | 3.28 |
| Example 4 | 81.5 | ● | 69.08 | 34.60 | 13.00 | 5.41 | 3.41 | 2.66 | 2.13 | 1.92 |
| Comparative Example 1 | 14.7 | ○ | 116.2 | 65.6 | 33.2 | 20.58 | 16.16 | 13.89 | 12.01 | 11.02 |
| Sorbosil AC 33 | 46 | ♦ | 111.80 | 75.26 | 45.18 | 26.96 | 18.94 | 14.77 | 11.26 | 9.48 |
| Zeodent 105 | <5 | — | 73.11 | 47.70 | 44.81 | 28.56 | 20.15 | 15.30 | 12.60 | 10.01 |

Figure 2:
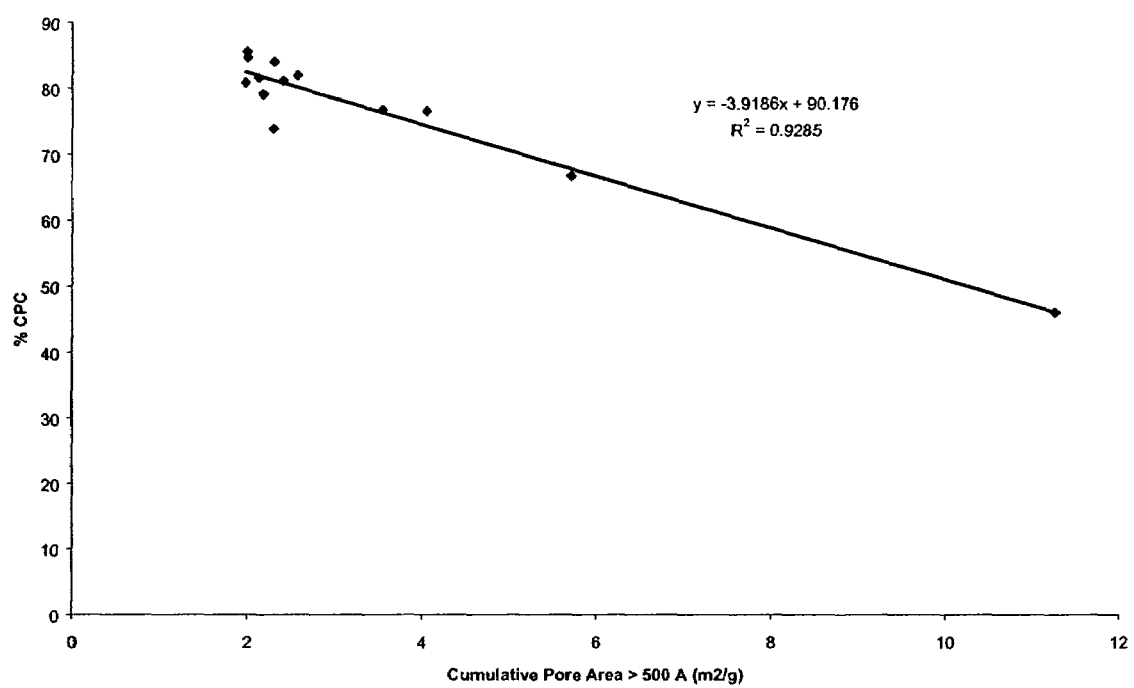
FIG. 2 is plot of % CPC and cumulative pore area ($m^2/g$) for pores with sizes greater than 500 Å, as measured from a series of silicas prepared as described in examples herein.

By plotting the cumulative surface area values as a function of pore diameter, a graphical representation of the data can be seen in FIG. 1. The cumulative surface area data is listed in Table 5 for each silica sample along with the symbol corresponding to each plot in FIG. 1 as applicable. FIG. 2 is a plot showing the correlation of the pore area for pores greater than 500 angstroms and CPC compatibility. Example 4 was replicated 9 times providing the cluster of data points shown on FIG. 2 illustrating reproducibility. When the cumulative pore area for pores greater than 500 Å was plotted versus CPC compatibility as in FIG. 2, a strong correlation was observed ($R^2$ values>90%). It can be seen from the surface area plots in FIGS. 1 and 2 for the different silica samples that the cumulative surface area (from pores greater than 500 Å) needs to be less than ~8 $m^2/g$ to obtain CPC compatibility values greater than ~55%.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. Precipitated silica comprising silica product particles having a porous surface, the silica particles having a cumulative surface area for all pores having diameters greater than about 500 Å of less than 8 m$^2$/g, as measured by mercury intrusion, a BET specific surface area of less than approximately 30 square meters per gram, and a percentage cetylpyridinium chloride (% CPC) Compatibility of greater than about 55%.

2. A silica product according to claim 1, wherein the silica particles have a percentage cetylpyridinium chloride (% CPC) Compatibility of greater than approximately 60%.

3. A silica product according to claim 1, wherein the silica particles have a % CPC Compatibility of greater than approximately 70%.

4. A silica product according to claim 1, wherein the silica particles have a % CPC Compatibility of greater than approximately 80%.

5. A silica product according to claim 1, wherein the silica particles have a median diameter of 1 to 20 micrometers.

6. A silica product according to claim 1, wherein the silica particles have a % CPC Compatibility value of approximately 55% to 95%.

7. A silica product according to claim 1, wherein the silica particles comprise silica aggregates or agglomerates individually comprising unitary clusters of a plurality of silica primary particles.

8. A silica product according to claim 1, the silica particles having a cumulative surface area for all pores having diameters greater than about 500 Å of less than 7 m$^2$/g, as measured by mercury intrusion.

9. Dentifrice, comprising:
a silica product comprising silica particles having a porous surface, the silica particles having a cumulative surface area for all pores having diameters greater than about 500 Å of less than 8 m$^2$/g, as measured by mercury intrusion, a BET specific surface area of less than approximately 30 square meters per gram, and a percentage cetylpyridinium chloride (% CPC) Compatibility of greater than about 55%.

10. Dentifrice according to claim 9, wherein the silica particles have a percentage cetylpyridinium chloride (% CPC) Compatibility of greater than approximately 60%.

11. Dentifrice according to claim 9, wherein the silica particles provide an increased flavor compatibility as compared to a dentifrice containing corresponding silica particles without said cumulative surface area and % CPC Compatibility.

12. Dentifrice according to claim 9, wherein the silica particles have a percentage cetylpyridinium chloride (% CPC) Compatibility of greater than approximately 70%.

13. Dentifrice according to claim 9, wherein the silica particles have a percentage cetylpyridinium chloride (% CPC) Compatibility of greater than approximately 80%.

14. Dentifrice according to claim 9, wherein the silica wherein the silica particles have a % CPC Compatibility value of approximately 55% to 95%.

15. Dentifrice according to claim 9, wherein the silica particles comprise aggregates or agglomerates individually comprised of clusters of a plurality of silica primary particles.

16. Dentifrice according to claim 9, further including an effective amount of at least one flavorant compatible with CPC.

17. Dentifrice according to claim 9, further including an effective amount of an anticaries compound comprising a fluoride ion source.

18. Dentifrice according to claim 9, further including an effective amount of antimicrobial agent.

19. Dentifrice according to claim 9, the silica particles having a cumulative surface area for all pores having diameters greater than about 500 A of less than 7 m$^2$/g, as measured by mercury intrusion.

20. Dentifrice, comprising:
a) antibacterial effective amount of cetylpyridinium chloride;
b) precipitated silica product comprising silica particles having a porous surface, the silica particles having a cumulative surface area for all pores having diameters greater than about 500 Å of less than 8 m$^2$/g, as measured by mercury intrusion, a BET specific surface area of less than approximately 30 square meters per gram, and a percentage cetylpyridinium chloride (% CPC) Compatibility of greater than about 55%.

21. Process for making precipitated silica product, comprising: a)
providing amorphous silica substrate particles having a median diameter of 1 to 100 micrometers;
b) depositing active silica onto surfaces of the silica substrate particles by acidulation of an alkali metal silicate in an aqueous medium, in which the substrate particles are dispersed, in an amount effective to provide a slurry of silica particles having a porous surface, the silica particles having a cumulative surface area for all pores having diameters greater than about 500 A of less than 8 m$^2$/g, as measured by mercury intrusion, and a percentage cetylpyridinium chloride (% CPC) Compatibility of greater than about 55%.

22. The process of claim 21, further comprising dewatering and drying the silica particles to a flowable finely divided particulate form.

23. The process of claim 21, wherein the providing of the silica particles comprises slurrying a dry flowable particulate form of the silica particles in an aqueous solution.

24. The process of claim 21, wherein the providing of the silica particles comprises forming the silica particles in situ by acidulation of an alkali metal silicate in an aqueous medium without drying below 20% water content before initiating step "b" thereof.

25. The process of claim 21, wherein the providing of the silica particles comprises providing silica aggregates or agglomerates individually comprising unitary clusters of a plurality of the amorphous silica primary particles.

26. The process of claim 21, wherein the silica particles have a % CPC Compatibility of greater than approximately 60%.

27. The process of claim 21, wherein the silica particles have a % CPC Compatibility of greater than approximately 70%.

28. The process of claim 21, wherein the silica particles have a % CPC Compatibility of greater than approximately 80%.

29. The process of claim 21, wherein the silica particles have a % CPC Compatibility within the range of about 55% to about 90%.

30. The product of the process of claim 21.

* * * * *